(12) United States Patent
Moribe et al.

(10) Patent No.: US 8,614,415 B2
(45) Date of Patent: Dec. 24, 2013

(54) DEFECT INSPECTION METHOD OF FINE STRUCTURE OBJECT AND DEFECT INSPECTION APPARATUS

(75) Inventors: Hideyuki Moribe, Tokyo (JP); Kenichi Matsumura, Tokyo (JP)

(73) Assignee: NEC Corporation, Tokyo (JP)

( * ) Notice: Subject to any disclaimer, the term of this patent is extended or adjusted under 35 U.S.C. 154(b) by 408 days.

(21) Appl. No.: 12/343,829

(22) Filed: Dec. 24, 2008

(65) Prior Publication Data

US 2009/0166517 A1 Jul. 2, 2009

(30) Foreign Application Priority Data

Dec. 28, 2007 (JP) .................................. 2007-341478

(51) Int. Cl.
G02F 1/01 (2006.01)

(52) U.S. Cl.
USPC ....................................................... 250/225

(58) Field of Classification Search
USPC ........ 250/225, 234, 578.1, 202, 459.1, 467.1, 250/548, 559.09, 559.4; 382/144, 145; 356/364–370, 237.3–237.5, 487
See application file for complete search history.

(56) References Cited

U.S. PATENT DOCUMENTS

| | | | |
|---|---|---|---|
| 6,389,185 B1 * | 5/2002 | Meise et al. | 385/11 |
| 6,690,469 B1 * | 2/2004 | Shibata et al. | 356/369 |
| 2003/0156280 A1 * | 8/2003 | Reinhorn | 356/237.2 |
| 2006/0262297 A1 * | 11/2006 | Matsui et al. | 356/237.5 |
| 2007/0206184 A1 * | 9/2007 | Uto et al. | 356/237.2 |

FOREIGN PATENT DOCUMENTS

| | | |
|---|---|---|
| JP | 63-12943 A | 1/1988 |
| JP | 1996005569 A | 1/1996 |
| JP | 9-28790 A | 2/1997 |
| JP | 9-292346 A | 11/1997 |
| JP | 9-292347 A | 11/1997 |
| JP | 2000066374 A | 3/2000 |
| JP | 2000155099 A | 6/2000 |
| JP | 2004515750 A | 5/2004 |
| JP | 2004301705 A | 10/2004 |
| JP | 2006343102 A | 12/2006 |
| JP | 2007192716 A | 8/2007 |
| JP | 2007232555 A | 9/2007 |
| JP | 2008532044 A | 8/2008 |

OTHER PUBLICATIONS

Japanese Office Action for JP2007-341478 issued Jan. 26, 2010.

* cited by examiner

*Primary Examiner* — Thanh Luu
*Assistant Examiner* — Renee Naphas
(74) *Attorney, Agent, or Firm* — Michael Dryja

(57) ABSTRACT

A method for forming an image of an object includes: illuminating sequentially a surface of the object arranged in the same shooting area using each of N (N is natural number equal to or more than two) polarized light beams, each of which has different property; scanning the surface using the each of N polarized light beams; and outputting the each of N polarized light beams reflected by the surface, the each of N polarized light beams passed-through the object or the each of N polarized light beams scattered by the surface, as an image signal.

19 Claims, 11 Drawing Sheets

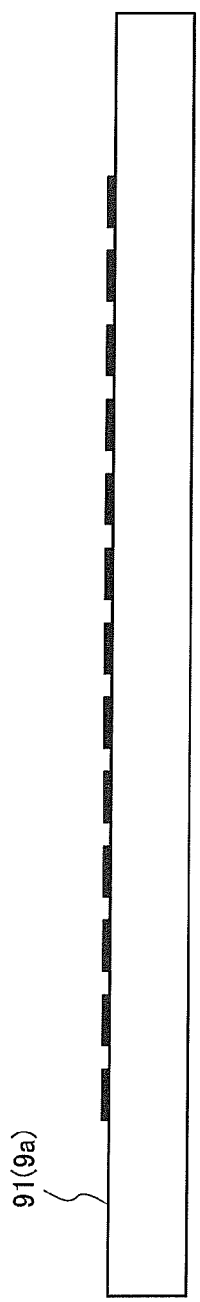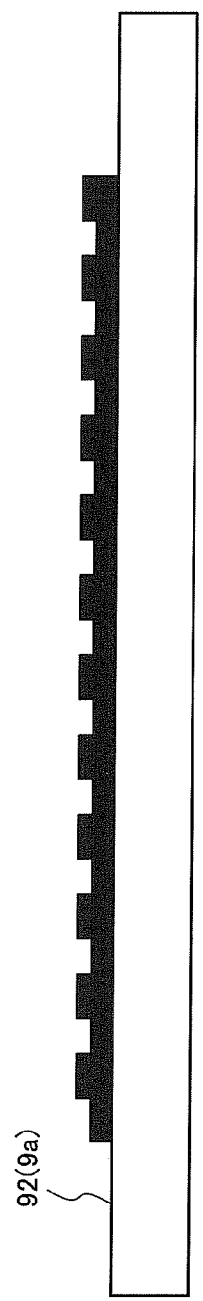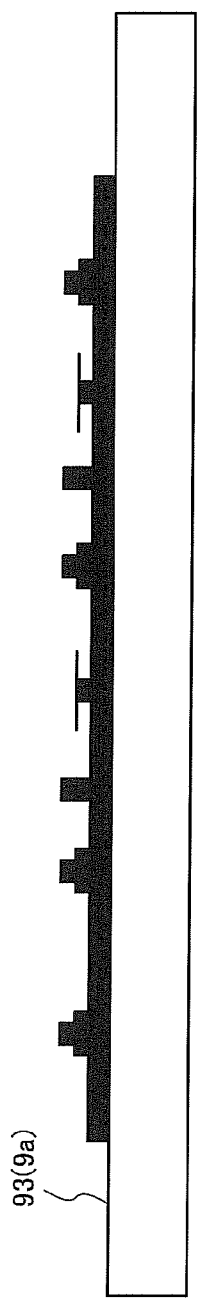

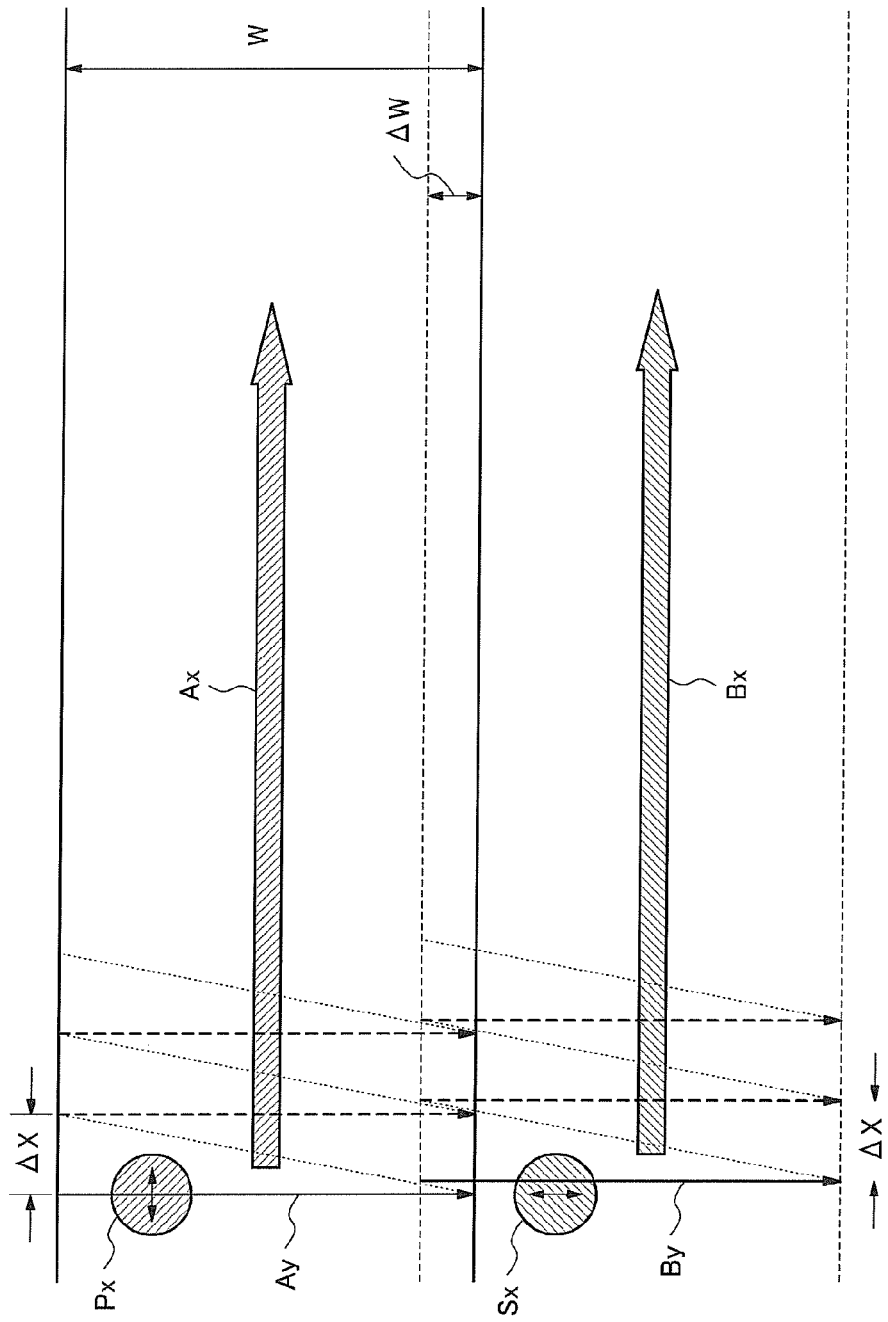

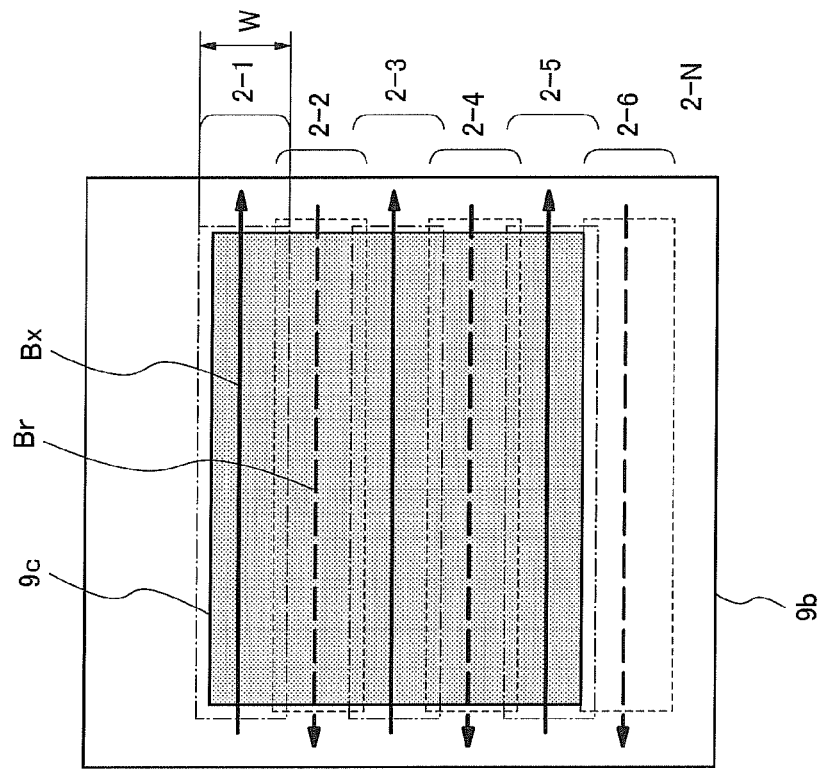
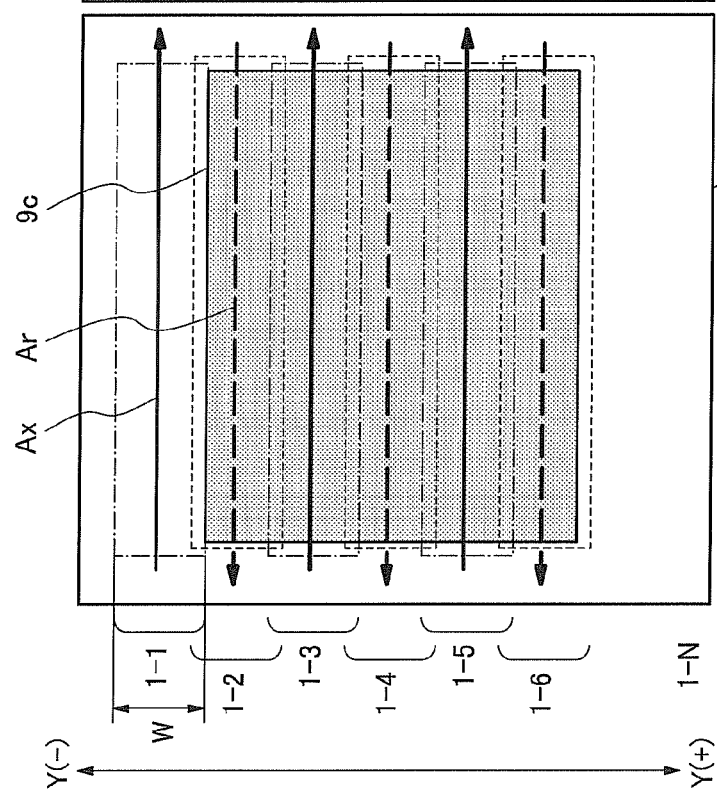

DEFECT INSPECTION METHOD OF FINE STRUCTURE OBJECT AND DEFECT INSPECTION APPARATUS

INCORPORATION BY REFERENCE

This application is based upon and claims the benefit of priority from Japanese Patent Application No. 2007-341478, filed on Dec. 28, 2007, the disclosure of which is incorporated herein in its entirety by reference.

TECHNICAL FIELD

The present invention relates to a method for forming an image of an object and an image forming apparatus.

BACKGROUND ART

A defect inspecting apparatus according to a method using an image of an optical microscope is well known. The defect inspecting apparatus according to the method inspects whether or not a defect of a shape of an inspection object exists and whether or not a foreign object exists on the inspection object by forming an image of a surface of the inspection object which is arranged on a stage. The inspection object indicates a reticle or a photo-mask on which fine patterns of a circuit and an element are formed. Moreover, the inspection object includes a fine structural object, like a minute electro-mechanical component called MEMS (Micro-Electro-Mechanical System) and an electronic device such as LSI (Large-Scale Integrated circuit) which are manufactured by downscaling the fine patterns of the circuit and the element and copying the fine patterns.

In the defect inspecting apparatus according to the method, it is emphasized to obtain an even and good microscope image in an observation view. Therefore, in order to illuminate the observation view uniformly and illuminate an inspection surface of the fine structural object, a light whose optical property is uniform in all directions, that is, a light in a non-polarized light (i.e. circularly-polarized light or randomly-polarized light) is preferable.

Furthermore, as micro-fabrication of LSI, MEMS or the like proceeds and miniaturization of the reticle pattern and photo mask pattern consequently proceeds, the defect inspecting apparatus having high resolving power which can clearly resolve a shape of the pattern on the inspection surface of the fine structural objects.

Resolving power $\epsilon$ of the optical microscope is represented as $\epsilon = k1 \times \lambda / NA$, where $\lambda$ is wavelength of a light and NA is numerical aperture of an objective lens (k1 is a fixed number determined on the basis of conditions of a light source). Accordingly, in order to resolve a fine surface structure, it is required to reduce the wavelength of the light and to increase NA of the objective lens. In order to reduce the wavelength of the light, a light source with high stable output power is required, and an optical imaging system having high accuracy which hardly deteriorates in short wavelength area and which can uniformly illuminate the observation view is also required.

From a viewpoint of optics, it is not easy to illuminate the observation view with uniform light intensity. Since the observation view is illuminated simultaneously, brightness becomes very low. Therefore, exposure time of a light receiving element (multi-element type image sensor, such as Charge Coupled Device (CCD) image sensor) has to be quite long, in order to obtain high Signal to Noise ratio (S/N).

Therefore, it is technically difficult to realize the optical imaging system with high accuracy by using a short wavelength light (e.g. wavelength of about 200 nm) which is technically available at the present time. Even if the optical imaging system is realized, the defect inspecting apparatus becomes very expensive. Realizing high NA is similar to the above case. That is, it is technically difficult to realize high NA even by using a liquid immersion lens or the like which becomes notable in recent years. Even if high NA is realized, the defect inspecting apparatus becomes very expensive. High cost for the defect inspecting apparatus can be one of causes of raising cost of the fine structural objects such as the reticle, the photo-mask, LSI and MEMS. Such things above mentioned are not preferable.

Japanese Patent Application Laid-Open No. 1996-005569 (hereinafter referred to as "patent document") discloses a scanning type particle measuring apparatus to resolve disadvantages of the defect inspecting apparatus using an imaging microscope method. In the particle measuring apparatus disclosed in the patent document, two kinds of laser beams including a p-polarized laser beam and an s-polarized laser beam vertically illuminate the same area of a wafer arranged on the stage simultaneously. A light reflected by the wafer is split into a p-polarized light component and an s-polarized light component by a polarized light beam splitter. The split p-polarized light component is converted into an electric signal by a light receiving part for the p-polarized light component. The split s-polarized light component is converted into an electric signal by a light receiving part for the s-polarized light component.

When a computer processes the two output signals sent thereto, it is detected whether or not a particle exists. Two kinds of laser beams scan the wafer with predetermined scanning width in cooperation with movement of the stage on which the wafer is arranged. Repeating the above mentioned operation, the laser beams scan the whole of the wafer surface. It is possible to carry out particle detecting over the whole of the wafer surface.

In the particle measuring apparatus disclosed in the patent document, since the laser beam scans the wafer surface, diameter of a converging spot of the laser beam is short compared with that of the defect inspection apparatus using the imaging microscope method. Therefore, the particle measuring apparatus gives very high brightness. Since problems regarding illumination intensity are resolved, high S/N ratio and high throughput are secured. Moreover, in the particle measuring apparatus, since scattered light intensity for diameter of each particle is different from each other according to polarization property, two kinds of the laser beams including the p-polarized laser beam and the s-polarized laser beam are used for measuring. As a result, particle measurement of each particle diameter can be performed with the highest sensitivity.

SUMMARY

An exemplary object of the present invention is to provide an image forming method and an image forming apparatus which can form an image of an object with high resolution and high sensitivity.

A method for forming an image of an object according to an exemplary aspect of the invention includes: illuminating sequentially a surface of the object arranged in the same shooting area using each of N (N is natural number equal to or more than two) polarized light beams, each of which has different property; scanning the surface using the each of N polarized light beams; and outputting the each of N polarized light beams reflected by the surface, the each of N polarized light beams passed-through the object or the each of N polarized light beams scattered by the surface, as an image signal.

An image forming apparatus according to another exemplary aspect of the invention includes: moving means for mounting an object thereon and moving the object; light outputting means for outputting a light beam; light beam splitting means for splitting the light beam into N (N is natural number equal to or more than two) polarized light beams, each of which has different property; scanning means for allowing the each of the N polarized light beams to radiate to a surface of the object and scan the surface; scanning control means for controlling the scanning means and the moving means to scan sequentially the surface in a predetermined shooting area using the each of N polarized light beams; and light detecting means for detecting the each of N polarized light beams reflected by the surface, the each of N polarized light beams passed-through the object or the each of N polarized light beams scattered by the surface, and for generating a image signal.

BRIEF DESCRIPTION OF THE DRAWINGS

Exemplary features and advantages of the present invention will become apparent from the following detailed description when taken with the accompanying drawings in which:

FIGS. 3A, 3B and 3C are schematic cross sectional views showing a cross sectional structure of various kinds of inspection objects;

FIG. 5 is a plan view showing the nonsimultaneous double-scanning operation;

FIGS. 6A and 6B are plan views showing an image processing method of the defect inspecting apparatus according to the first exemplary embodiment of the present invention;

EXEMPLARY EMBODIMENT

Exemplary embodiments of the present invention will now be described in detail in accordance with the accompanying drawings.

1. First Exemplary Embodiment

First, property of a polarized light will be described. When a beam converged on a surface of an inspection object is a linearly polarized light, following phenomena are occurred, depending on a direction of polarization. "Direction of polarization" is the direction of the polarization plane of the linearly polarized light.

(1) When a beam is converged by using a lens with high NA, an elliptical beam which spreads in the direction of polarization of the linearly polarized light is generated.

(2) When the beam is converged by using the lens with high NA, if incident angle is large, both difference between transmissivity of a p-polarized light and that of an s-polarized light, of which directions of polarization are orthogonal to each other, and difference between reflectance of the p-polarized light and that of the s-polarized light are large. The p-polarized light and the s-polarized light are linearly polarized lights and the directions of polarization of the two lights are perpendicular to each other. That is, when the incident angle is large, the transmissivity of the p-polarized light is larger than that of the s-polarized light. On the other hand, the reflectance of the s-polarized light is larger than that of the p-polarized light.

Further, a relation between $\theta$ and NA is represented as the formula, $NA = n \cdot \sin \theta$ where n is refractive index of medium between an object and a lens and $\theta$ is the largest incident angle. Accordingly, it is possible to consider based on NA instead of the incident angle.

(3) In a fine slit or a fine line and space (L/S) pattern (diffraction grating or the like) whose size is almost equal to a wavelength, high transmissivity values of the polarized lights are given in the order of a linearly polarized light whose direction of polarization is parallel to a direction of the slit, a circularly polarized light and a linearly polarized light whose direction of polarization is orthogonal to the direction of the slit. That is, when transmissivity of the linearly polarized light whose direction of polarization is parallel to the direction of the slit is expressed as T1, transmissivity of the circularly polarized light is expressed as T2, and transmissivity of the linearly polarized light whose direction of polarization is orthogonal to the direction of the slit is expressed as T3, $T1 > T2 > T3$.

The above-mentioned magnitude relations mean that resolving power in the direction orthogonal to the direction of polarization of the linearly polarized light is high and indicate that there exists the most suitable property of polarized light depending on a direction of an inspection pattern.

Figure 1:
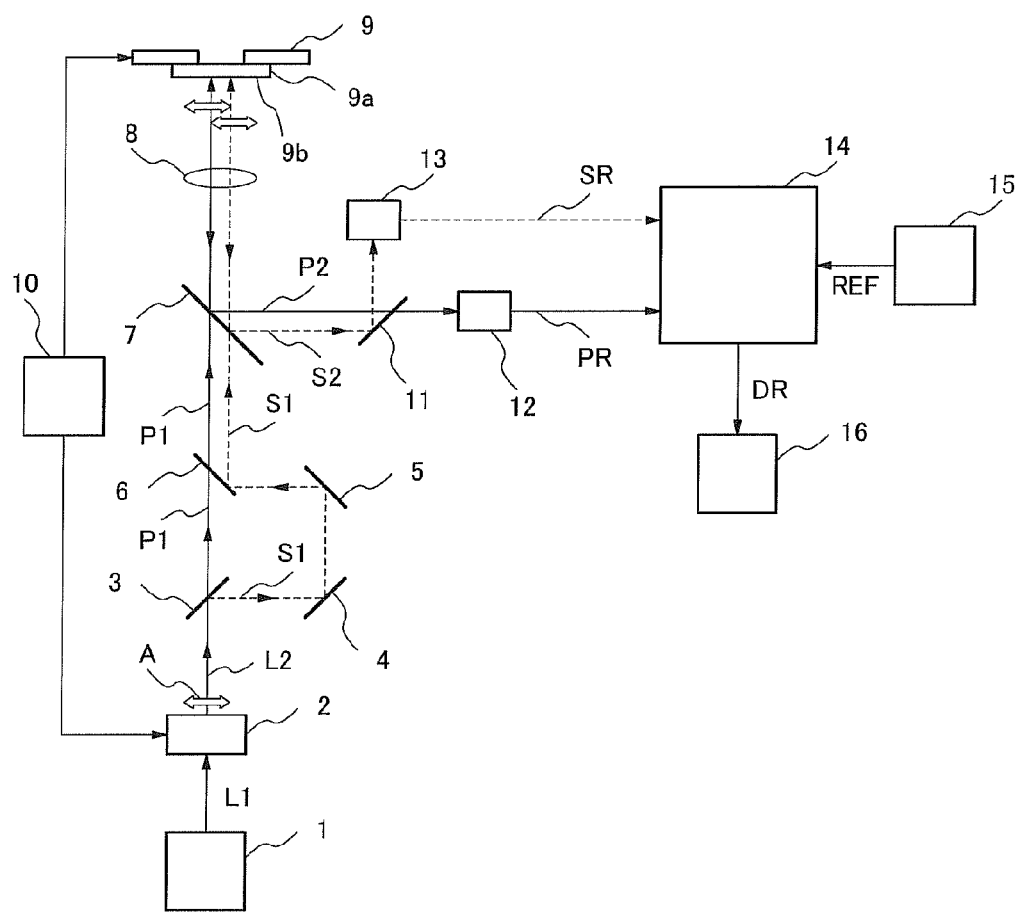
FIG. 1 is a block diagram showing a schematic configuration of a defect inspecting apparatus for a fine structural object according to a first exemplary embodiment of the present invention.
Figure 2A:
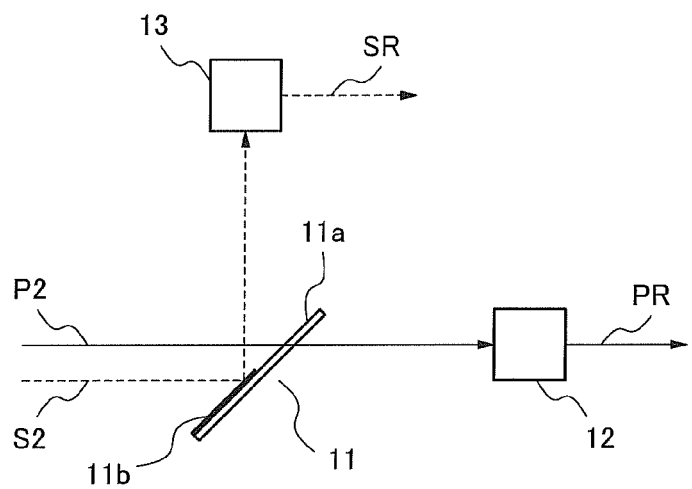
FIG. 2A is a schematic enlarged view showing an operation of a split mirror which is included in an optical system of the defect inspecting apparatus according to the first exemplary embodiment of the present invention.
Figure 2B:
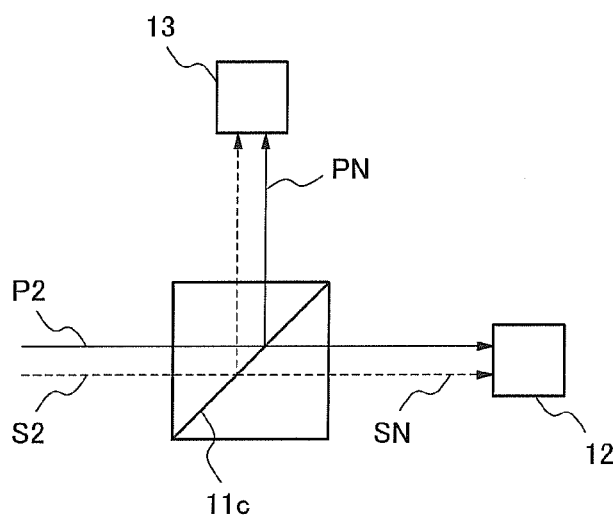
FIG. 2B is a schematic enlarged view showing an operation of a polarized light beam splitter which is included in an optical system of a defect inspecting apparatus according to a fourth exemplary embodiment of the present invention.
Figure 4:
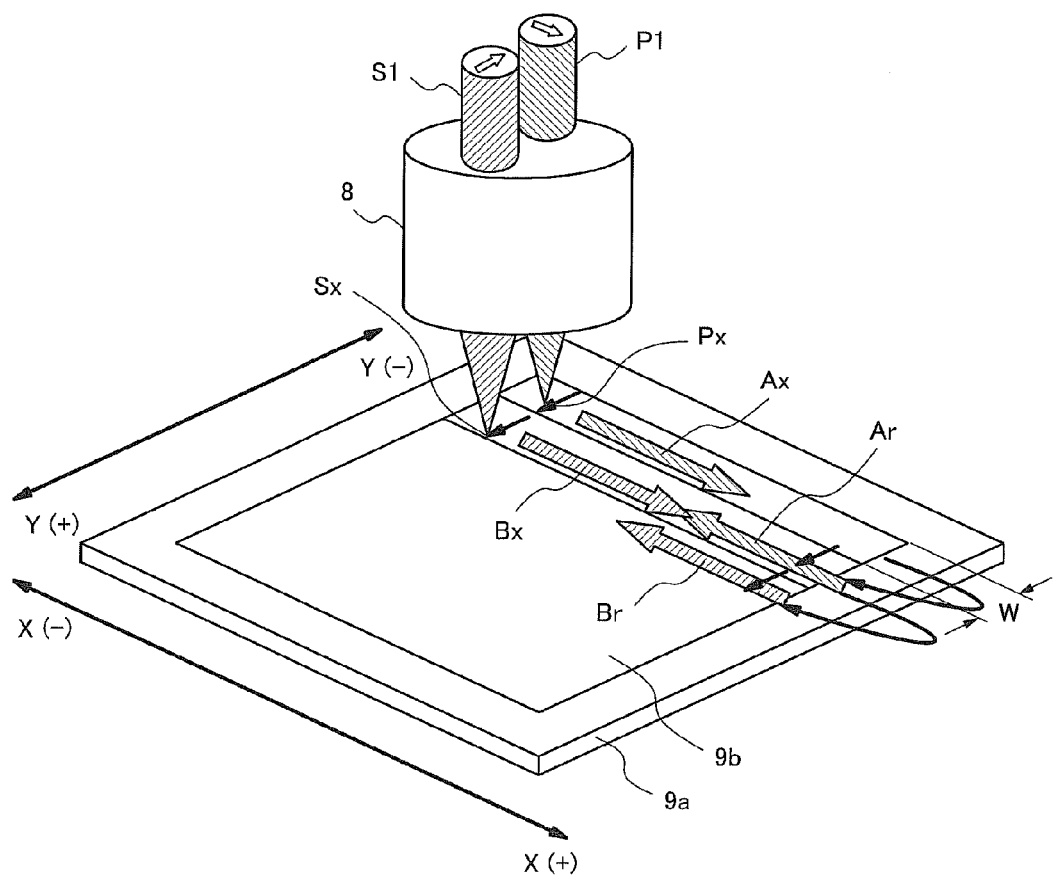
FIG. 4 is a perspective view showing schematically a nonsimultaneous double-scanning operation of the defect inspecting apparatus using a p-polarized light and an s-polarized light according to the first exemplary embodiment of the present invention.

A first exemplary embodiment of the present invention will be described in detail with reference to drawings. FIG. 1 is a block diagram showing a schematic configuration of a defect inspecting apparatus which inspects a defect of a fine structural object according to a first exemplary embodiment of the present invention. FIGS. 2A and 2B are schematic enlarged views showing an operation of a split mirror which is included in an optical system of the defect inspecting apparatus according to the first exemplary embodiment of the present invention. FIGS. 3A, 3B and 3C are schematic cross sectional views showing various kinds of inspection objects. FIG. 4 is a perspective view showing schematically a nonsimultaneous double-scanning operation of the defect inspecting apparatus using the p-polarized light and the s-polarized light according to the exemplary embodiment of the present invention. FIG. 5 is a plan view showing the nonsimultaneous double-scanning operation. FIG. 6 is a plan views showing an image processing method of the defect inspecting apparatus according to the first exemplary embodiment of the present invention.

An entire configuration of the defect inspection apparatus according to the exemplary embodiment of the present invention will be described. The defect inspection apparatus is an inspection apparatus using a scanning type reflection microscope method which inspects whether or not any defect exists in an inspection area through photographing a reflection image of the fine structural object, that is, the inspection object. As shown in FIG. 1, the defect inspecting apparatus includes a light source 1, a deflection scanning means 2, a first polarized light beam splitter 3, mirrors 4 and 5, a second polarized light beam splitter 6, a semi-transparent mirror 7 and an objective lens 8. Further, the defect inspecting apparatus includes a XY stage 9, a scanning control unit 10, a split mirror 11, photoelectric converters 12 and 13, an image processing system 14, a reference image storing unit 15 and an inspection data storing unit 16. The deflection scanning means 2 is an example of a scanning means. The first and the second polarized light beam splitters 3 and 6 are examples of a light beam splitting means. The scanning control circuit 10 is an example of a scanning control means. The photoelectric converters 12 and 13 are examples of a detection signal generating means. The image processing system 14 is an example of an image processing means.

Next, each part of the defect inspection apparatus will be described. The light source 1 outputs a light beam L1. According to the exemplary embodiment of the present invention, it is desirable to decrease diameter of a light converging spot which illuminates a surface of the inspection object in order to enhance resolving power of the scanning type optical microscope. Therefore, a short wavelength light source is applied to the light source 1. Moreover, in order to improve S/N, a light source with high brightness is required. Accordingly, it is preferable to employ a far ultraviolet laser whose wavelength is 266 nm as the light source 1. Moreover, it is possible to employ a far ultraviolet laser of wavelength 253 nm or 199 nm which can output a light beam with further short wavelength as the light source 1, if needed.

The deflection scanning means 2 includes a scanning optical system such as an acoustic-optical deflecting unit, a polygon mirror and a galvano mirror, a beam expander, a half wavelength plate or the like. The deflection scanning means 2 converts the incident light beam L1 from the light source 1 into a beam having required beam diameter, deflects the beam at high speed and outputs the beam as a light beam L2. The deflection scanning means 2 scans an inspection object surface 9b at predetermined scanning width by deflecting the light beam L1.

The first polarized light beam splitter 3 splits the light beam L2 into a p-polarized light beam P1 and an s-polarized light beam S1. That is, the first polarized light beam splitter 3 allows the p-polarized light component P1 of the light beam L2 to pass through and reflects the s-polarized light component S1 of the light beam L2. As a result, the light beam L2 is divided into the p-polarized light beam P1 and the s-polarized light beam S1. The s-polarized light beam S1 is reflected by the mirrors 4 and 5, and a travelling direction of the s-polarized light beam S1 changes by 180 degrees. The s-polarized light beam S1 enters a back surface of the second polarized light beam splitter 6.

The second polarized light beam splitter 6 allows the p-polarized light beam P1, which passes through the first polarized light beam splitter 3 and enters a surface of the second polarized light beam splitter 6, to pass through. Moreover, the second polarized light beam splitter 6 reflects the s-polarized light beam S1 which is reflected by the first polarized light beam splitter 3 and the mirrors 4 and 5 in sequence and enters the back surface of the second polarized light beam splitter 6. The second polarized light beam splitter 6 combines the p-polarized light beam P1 and the s-polarized light beam S1 to form a pair of beams. Combining the p-polarized light beam P1 and the s-polarized light beam S1, the second polarized light beam splitter 6 deviates the p-polarized light beam P1 and the s-polarized light beam S1 in a scanning direction (a direction indicated by an arrow A in FIG. 1) of the deflection scanning means 2 by a distance corresponding to the scanning width. The scanning width can be changed appropriately according to a size of the inspection pattern. In the exemplary embodiment of the present invention, the scanning width on the inspection object surface 9b ranges from 40 μm to 70 μm. The inspection object surface 9b means a surface of an inspection object 9a on which the pattern is formed. Since the scanning width may be set in an appropriate range according to the inspection object, the scanning width is not limited to the above-mentioned range.

The semi-transparent mirror 7 allows a part of the p-polarized light beam P1 and a part of the s-polarized light beam S1, which are combined and are deviated at the distance of the scanning width, to pass through. That is, the semi-transparent mirror 7 allows the p-polarized light beam P1 and the s-polarized light beam S1 to pass through semi-transparently (translucently). The semi-transparent mirror 7 reflects a part of reflection light P2 and S2 reflected by the inspection object surface 9b and changes a travelling direction of the reflection light P2 and S2. As shown in FIG. 4, the objective lens 8 lets the incident p-polarized light beam P1 and the incident s-polarized light beam S1 converge on the inspection object surface 9b. The objective lens 8 includes a large aperture. For example, NA of the objective lens 8 is not smaller than 0.8. The objective lens 8 forms a minute light converging spot Px of the p-polarized light beam P1 and a minute light converging spot Sx of the s-polarized light beam S1 on the inspection object surface 9b of the inspection object 9a. Each diameter of the light converging spots Px and Sx is from 0.3 μm to 0.4 μm.

As shown in FIG. 3A, a fine structural object 91 such as a reticle or a photo-mask used in photolithography method which includes a shape almost equal to a plane is exemplified as the inspection object 9a. As shown in FIG. 3B, a fine structural object 92 having a minute and deep gap like an extreme ultra violet (EUV) lithography mask used in EUV lithography is exemplified as other example. Moreover, as shown in FIG. 3C, a fine three-dimensional structural object 93 or the like on the plane like MEMS is also an example of the inspection object 9a. The fine structural objects 91, 92 and the fine three-dimensional structural object 93 are examples of the inspection object 9a. Therefore, the inspection object 9a is not limited to the examples above described.

The XY stage 9 includes a drive system (not shown) on which the inspection object 9a is arranged and which moves in a two-dimensional surface including an X direction and a Y direction. The scanning control unit 10 controls the deflection scanning means 2 and the drive system of the XY stage 9. The deflection scanning means 2 scans the inspection object surface 9b in direction Y(+) using the light converging spot Px of the p-polarized light and the light converging spot Sx of the s-polarized light which are away from each other by the distance corresponding to the scanning width W (FIGS. 4 and 5). As shown in FIGS. 4 and 5, for example, the scanning control unit 10 moves the line of the scanning by the deflection scanning means 2 to direction X(+) by a scanning pitch ΔX. The deflection scanning means 2 scans a one-dimensional inspection area whose length is corresponding to the scan width W from a scan starting position to a scan terminating position in a direction Y(+) (Ay and By directions in FIG. 5) using the light converging spot Px of the p-polarized light and the light converging spot Sx of the s-polarized light. Moreover, the scanning control unit 10 controls the drive system of the XY stage 9, and move the inspection object 9a in a direction X(−) when a scanning position moves to a next scan starting position from the scan terminating position. Therefore, the light converging spot Px of the p-polarized light and the light converging spot Sx of the s-polarized light move relatively in directions indicated by arrows Ax and Bx (FIGS. 4 and 5) respectively. When the operations are repeated, the whole two-dimensional inspecting area (FIG. 6) is scanned by two kinds of the light converging spots Px and Sx whose direction of polarization are orthogonal to each other. According to the exemplary embodiment of the present invention, as mentioned below, "nonsimultaneous double-scanning" is carried out on each inspection area (FIGS. 4 and 6). The nonsimultaneous double-scanning is a double-scanning which includes the polarized light beam scanning by using the light converging spot Px of the p-polarized light and the polarized light beam scanning by using the light converging spot Sx of the s-polarized light.

The split mirror 11 is arranged at a confocal position with respect to the inspection object surface 9b of the inspection object 9a, and forms a confocal optical system together with the inspection object 9a, the objective lens 8 and the semi-transparent mirror 7. In the confocal optical system, the p-polarized light beam P1 and the s-polarized light beam S1 are outputted toward the inspection object surface 9b of the inspection object 9a by the spatial distance of the scanning width W therebetween, and form the light converging spot Px and the light converging spot Sx respectively. And the reflection light P2 of the p-polarized light beam P1 from the light converging spot Px and the reflection light S2 of the s-polarized light beam S1 from the light converging spot Sx enter the split mirror 11 by the spatial distance therebetween. As shown in FIG. 2A, the split mirror 11 includes a transmissive area 11a and a reflection area 11b. The transmissive area 11a allows the reflection light P2 of the p-polarized light beam P1 to pass through. The reflection light P2 of the p-polarized light beam P1 is reflected by the inspection object surface 9b of the inspection object 9a, goes back through the objective lens 8, is reflected by the semi-transparent mirror 7 and afterward, enters the split mirror 11. The reflection area 11b reflects the entering reflection light S2 of the s-polarized light beam S1. The split mirror 11 further certainly and spatially splits the reflection light P2 of the p-polarized light beam P1 and the reflection light S2 of the s-polarized light beam S1 which enter with the spatial distance therebetween.

The photoelectric converters 12 and 13 include a photodiode, a photomultiplier or the like. As shown in FIG. 2A, the photoelectric converter 12 receives the reflection light P2 of the p-polarized light beam P1 which passes the transmissive area 11a of the split mirror 11 and generates a p-reflection image detecting signal PR which is an electric signal. The photoelectric converter 13 receives the reflection light S2 of the s-polarized light beam S1 which is reflected in the reflection area 11b of the split mirror 11 and generates an s-reflection image detecting signal SR which is an electric signal. The reference image storing unit 15 stores a reference image REF as design data. The image processing system 14 photographs two kinds of two-dimensional reflection images (p-reflection image and s-reflection image) as a real image, based on the p-reflection image detecting signal PR and the s-reflection image detecting signal SR provided by the photoelectric converters 12 and 13 respectively. The image processing system 14 compares the photographed real image with the reference image as the design data, carries out image processing to calculate difference therebetween and judges whether or not any defect exists in the inspection object 9a. The inspection data storing unit 16 stores an inspection result DR on whether or not the defect exists in the inspection object 9a.

With reference to FIGS. 1 to 6, an operation of the defect inspection apparatus according to the exemplary embodiment of the present invention will be described. The light beam L1 outputted from the light source 1 is converted into a beam having desired beam diameter and is fast deflected by the deflection scanning means 2. Then, the light beam L1 travels in a light path as the light beam L2. The light beam L2 which is deflected at high speed enters the deflection scanning means 2 and is split into the p-polarized light beam P1 and the s-polarized light beam S1. The split s-polarized light beam S1 is reflected by the mirrors 4 and 5 to reach the second polarized light beam splitter 6. The p-polarized light beam P1 and the s-polarized light beam S1 are combined by the second polarized light beam splitter 6 as a pair of beams. Then, the p-polarized light beam P1 and the s-polarized light beam S1 are spaced by the distance corresponding to the scanning width W in a scanning direction of the deflection scanning means 2 (FIG. 1, FIG. 5 and FIG. 6). The p-polarized light beam P1 and the s-polarized light beam S1 which are combined each other are converged by the objective lens 8, and the minute light converging spot Px of the p-polarized light and the minute light converging spot Sx of the s-polarized light each having diameter of 0.3 μm to 0.4 μm are generated. Then, the p-polarized light beam P1 and the s-polarized light beam S1 which are combined illuminate the inspection object surface 9b.

Here, as shown in FIGS. 4 and 5, the light converging spots Px of the p-polarized light and the light converging spots Sx of the s-polarized light whose directions of polarization are orthogonal to each other are located by the distance corresponding to the scanning width W, for example, 40 μm to 70 μm in the scanning direction (direction indicated by the arrow Y(+)). The light converging spot Px of the p-polarized light and the light converging spot Sx of the s-polarized light illuminate and scan the inspection object surface 9b. That is, the light converging spot Px of the p-polarized light scans the inspection object surface 9b in the direction indicated by the arrow Ay. The light converging spot Sx of the s-polarized light scans the inspection object surface 9b in the direction indicated by the arrow By (direction parallel to the direction indicated by the arrow Ay), while being away from the light converging spot Px of the p-polarized light by the distance corresponding to the scanning width W in the scanning direction (direction indicated by the arrow Y(+)). Actually, it is preferable to overlap the scanning area of the light converging spot Px of the p-polarized light and the scanning area of the light converging spot Sx of the s-polarized light each other by width of a boundary area ΔW to completely scan the whole of the inspection area, as shown in FIG. 5. Therefore, in a precise sense, as shown in FIG. 5, the distance between the light converging spot Px of the p-polarized light and the light converging spot Sx of the s-polarized light is a value which is given by subtracting the width of overlap area ΔW from the scanning width W in the scanning direction (direction indicated by the arrow Y(+)).

The scanning control unit 10 controls the drive by the deflection scanning means 2 and the drive by the XY stage 9. Accordingly, the scanning control unit 10 controls the light converging spots Px and Sx whose directions of polarization are orthogonal to each other to scan the inspection object surface 9b of the inspection object 9a in sequence s-polarized (FIGS. 4 and 6). The nonsimultaneous double-scanning is carried out for each inspection area, that is, the scanning using the light converging spot Px of the p-polarized light (p-polarized light beam scanning Ay) and the scanning using the light converging spot Sx of the s-polarized light (s-polarized light beam scanning By) is carried out for each inspection area (FIGS. 4 and 6). As shown in FIG. 5, the p-polarized light beam scanning Ay using the light converging spot Px of the p-polarized light and the s-polarized light beam scanning By using the light converging spot Sx of the s-polarized light are carried out repeatedly while the spots Px and Sx are spaced each other by a distance of the scanning width of (W−ΔW). Moreover, whenever the p-polarized light beam scanning Ay and the s-polarized light beam scanning By are performed, the scanning control unit 10 controls the drive system of the XY stage 9 to move the inspection object 9a in the direction X(−) which is orthogonal to the scanning direction Y(+). As a result, the light converging spot Px of the p-polarized light and the light converging spot Sx of the s-polarized light move relatively on the inspection object surface 9b in the directions indicated by the arrows Ax and Bx respectively which are parallel and opposite to the direction X(−), as shown in FIGS. 4 and 5 (i.e. feeding). As a result, a two-dimensional p-polarized light beam scanning Ay-Ax and a two-dimensional s-polarized light beam scanning By-Bx are carried out on the inspection object surface 9b.

Then, a laser interferometer (not illustrated) measures a moving distance of the XY stage 9 in the direction X(−). The scanning control unit 10 judges whether or not the light converging spot Px of the p-polarized light and the light converging spot Sx of the s-polarized light reaches a one-dimensional inspection area (scanning position) for next scanning, based on the measured data by the laser interferometer. The scanning control unit 10 determines scanning start timing of each of the polarized light beam scanning Ay-By. Specifically, FIG. 5 shows that each of the polarized light beam scanning Ay-By is carried out at the scanning pitch Δx (for example, 100 nm). In such case, whenever the laser interferometer measures that the XY stage 9 moves Δx (100 nm), the scanning control unit 10 instructs the deflection scanning means 2 to start scanning.

When the two-dimensional p-polarized light beam scanning Ay-Ax and the two-dimensional s-polarized light beam scanning By-Bx reach a termination edge of the two-dimensional inspection area of the inspection object 9a as shown in FIG. 4, the scanning control unit 10 controls the drive system of the XY stage 9. Then, the scanning control unit 10 moves the inspection object 9a on the XY stage 9 in the direction Y(−) by the distance of the scanning width (i.e. a distance of (W−ΔW)) in stages. As a result, as shown in FIG. 4, the light converging spot Px of the p-polarized light and the light converging spot Sx of the s-polarized light move relatively on the inspection object surface 9b to a next starting edge of the two-dimensional inspection area.

Afterward, while moving the XY stage 9 in the direction X(+) opposite to the previous scanning direction X(−), the scanning control unit 10 repeatedly performs the p-polarized light beam scanning Ay and the s-polarized light beam scanning By. As a result, the light converging spot Px of the p-polarized light and the light converging spot Sx of the s-polarized light are fed relatively on the inspection object surface 9b in the directions indicated by arrows Ar and Br opposite to directions indicated by the arrows Ax and Bx respectively, as shown in FIG. 4. As a result, the two-dimensional p-polarized light beam scanning Ay-Ar and the s-polarized light beam scanning By-Br on the inspection object surface 9b are carried out. After that, the same operation above described is repeatedly performed, and the whole of the inspection area is scanned on the inspection object surface 9b in a meandering fashion.

FIGS. 6A and 6B are schematic views showing that the p-polarized light beam scanning Ay-Ax and Ay-Ar and the s-polarized light beam scanning By-Bx and By-Br are performed on the inspection object surface 9b in a meandering fashion (e.g. three-time reciprocating scans). FIG. 6A shows the meandering scanning by the light converging spot Px of the p-polarized light. FIG. 6B shows the meandering scanning by the light converging spot Sx of the s-polarized light. The light converging spot Px of the p-polarized light is formed on an upper side of the light converging spot Sx of the s-polarized light in FIG. 6 and away from the light converging spot Sx approximately with the distance (W−ΔW) corresponding to the scanning width W. Therefore, the light converging spot Px of the p-polarized light only scans a partial area, such as a scanning area 1-1 (FIG. 6A) on which the p-polarized light beam scanning Ay-Ax is performed as first-time scanning. Similarly, the light converging spot Sx of the s-polarized light is formed on a lower side of the light converging spot Px of the p-polarized light in FIG. 6 and away from the light converging spot Px with the distance (W−ΔW) approximately corresponding to the scanning width W. Therefore, only the light converging spot Sx of the s-polarized light scans a partial area, such as a scanning area 2-6 (FIG. 6) on which the s-polarized light beam scanning By-Br is performed as the last-time scanning.

The scanning area excluding the scanning areas 1-1 and 2-6 is double-scanned by the p-polarized light beam scanning Ay-Ax and Ay-Ar, and the s-polarized light beam scanning By-Bx and By-Br as a double-scanning area. The double-scanning area is substantial inspection area 9c. As shown in FIG. 6A, the second time, the third time, . . . , and the sixth time p-polarized light beam scanning Ay-Ax and Ay-Ar are carried out respectively on the scanning areas 1-2, 1-3, . . . , and 1-6 in a sectioned fashion. Moreover, as shown in FIG. 6B, the first time, the second time, . . . , and the fifth time s-polarized light beam scanning By-Bx and By-Br are carried out respectively on the scanning areas 2-1, 2-2, . . . , and 2-5 in a sectioned fashion.

Since the nonsimultaneous double-scanning are carried out by using the light converging spot Px of the p-polarized light and the light converging spot Sx of the s-polarized light through the operation mentioned above, the p-polarized light reflection image reflecting property of the p-polarized light and the s-polarized light reflection image reflecting property of the s-polarized light are obtained. In the defect inspection process, the p-polarized light reflection image photographed using the p-polarized light and the s-polarized light reflection image photographed using the s-polarized light are compared, and one reflection image having higher resolving power than that the other has is adopted. Accordingly, whether or not defect of shape of the inspection object (fine structural object) 9a and a foreign object attached to the inspection object 9a exist is inspected with high resolution and high sensitivity.

Next, a method of image processing will be described with reference to FIGS. 6A and 6B. The p-polarized light beam scanning Ay-Ax and the s-polarized light beam scanning By-Bx as the first time scanning are carried out simultaneously in the respective scanning areas (two-dimensional inspection area) 1-1 and 2-1. Then, the p-polarized light reflection image and the s-polarized light reflection image are obtained simultaneously. However, the p-polarized light reflection image and the s-polarized light reflection image are not reflection images of the same scanning area. That is, as mentioned above, the scanning area 1-1 (FIG. 6A) is not scanned by the light converging spot Sx of the s-polarized light. Therefore, only the p-polarized light reflection image which reflects the scanning area 2-1 is stored in the image processing system 14 (FIG. 1).

The second time p-polarized light beam scanning Ay-Ar and the second time s-polarized light beam scanning By-Br are feeding processes in a returning direction performed by the XY stage 9. The second time p-polarized light beam scanning Ay-Ar and the second time s-polarized light beam scanning By-Br are carried out simultaneously in the respective scanning areas 1-2 and 2-2, and the p-polarized light reflection image and the s-polarized light reflection image are photographed simultaneously. The p-polarized light reflection image which reflects the scanning area 1-2 in the second time scanning and the s-polarized light reflection image which reflects the scanning area 2-1 in the first time scanning are images which reflects the same inspection area. Accordingly, a die-to-die inspection, a die-to-database inspection, a combination inspection, and a time difference inspection are carried out by using of the p-polarized light reflection image which reflects the scanning area 1-2 and the s-polarized light reflection image which reflects the stored scanning area 2-1.

A photo-mask (reticle) for semiconductor manufacturing is used when a circuit pattern is transferred on the semiconductor wafer and exposure is performed, that is, when photolithography is carried out. In order to manufacture a lot of integration circuits with the same circuit pattern from one semiconductor wafer, an array of the same circuit pattern to be called a die on the photo-mask (reticle). The die-to-die inspection is a method in which a defect of the die is detected through comparing actual images of two dies having the same pattern. The die-to-die inspection may be carried out through observing actual images of two dies which are displayed on the screen of display apparatus with the naked eye.

The die-to-database inspection is a method in which the reflection image as an actual image of the die is compared with the reference image (the reference pattern) REF which is produced based on CAD design data. That is, when the die-to-database inspection is carried out by the defect inspection apparatus according to the exemplary embodiment of the present invention, the actual image of the die is compared with the reference image REF read from the reference image storing unit 15 (FIG. 1), and a difference between the two images is figured out. Then, a defect of the inspection object 9a is detected based on the obtained differential image. The combination inspection is an inspection in which both of the die-to-die inspection and the die-to-database inspection are performed. The time difference inspection is an inspection in which an image data of the die which is photographed and stored is compared with a die image which is photographed again afterward. That is, the time difference inspection is carried out at different times each other.

The s-polarized light reflection image which reflects the scanning area 2-2 in the second time scanning and the p-polarized light reflection image of the scanning area 1-3 in next time (i.e. the third time) scanning, is used for the defect inspection for the scanning area 2-2 which is identical to the scanning area 1-3. Therefore, the s-polarized light reflection image of the scanning area 2-2 is stored in the image processing system 14 (FIG. 1). Afterward, the inspection processing mentioned above is repeated.

As mentioned above, it is possible to judge whether or not a defect exists with the naked eye. Then, the defect inspection apparatus only displays the photographed image. That is, it is required that the defect inspection apparatus includes the display apparatus to display the whole of the image of the inspection object surface 9b by using the p-reflection image detecting signal PR and the s-reflection image detecting signal SR. It is possible that the display apparatus includes in the image processing system 14. It is not necessary that the display apparatus is included in the defect inspection apparatus, since an external display apparatus may be utilized as the display apparatus.

The image processing system 14, the reference image storing unit 15 and the inspection data storing unit 16 may be replaced by an external processing apparatus such as a computer. In such a case, the p-reflection image detecting signal PR and the s-reflection image detecting signal SR can enter the external processing apparatus which processes these signals.

Accordingly, the defect inspection apparatus in FIG. 1 does not necessarily include the image processing system 14, the reference image storing unit 15 and the inspection data storing unit 16.

Moreover, two kinds of polarized lights whose properties are different from each other, that is, the p-polarized light beam P1 and the s-polarized light beam S1 may be entered from outside. In such a case, it is not necessary to split the light beam L1 into the p-polarized light beam P1 and the s-polarized light beam S1. Accordingly, the light source 1, the first polarized light beam splitter 3, the mirrors 4 and 5 and the second polarized light beam splitter 6 become unnecessary. When the required resolving power is low, the objective lens 8 is also unnecessary. When an inspection area is small, it is possible to perform the inspection only with the scanning by the deflection scanning means 2. In such a case, the scanning control unit 10 is unnecessary. Moreover, the reflection light P2 and S2 can be outputted as a light signal without photoelectrical conversion. In such a case, the split mirror 11 and the photoelectric converters 12 and 13 are unnecessary.

Figure 11:
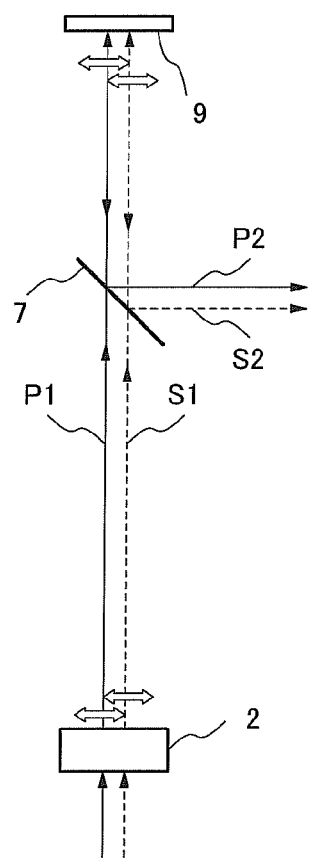
FIG. 11 is a block diagram showing components indispensable to the defect inspecting apparatus for the fine structural object according to the first exemplary embodiment of the present invention.

Accordingly, the minimum configuration of the defect inspection apparatus is shown in FIG. 11. The defect inspection apparatus shown in FIG. 11 includes the deflection scanning means 2 and the semi-transparent mirror 7.

2. A Second Exemplary Embodiment

Figure 7:
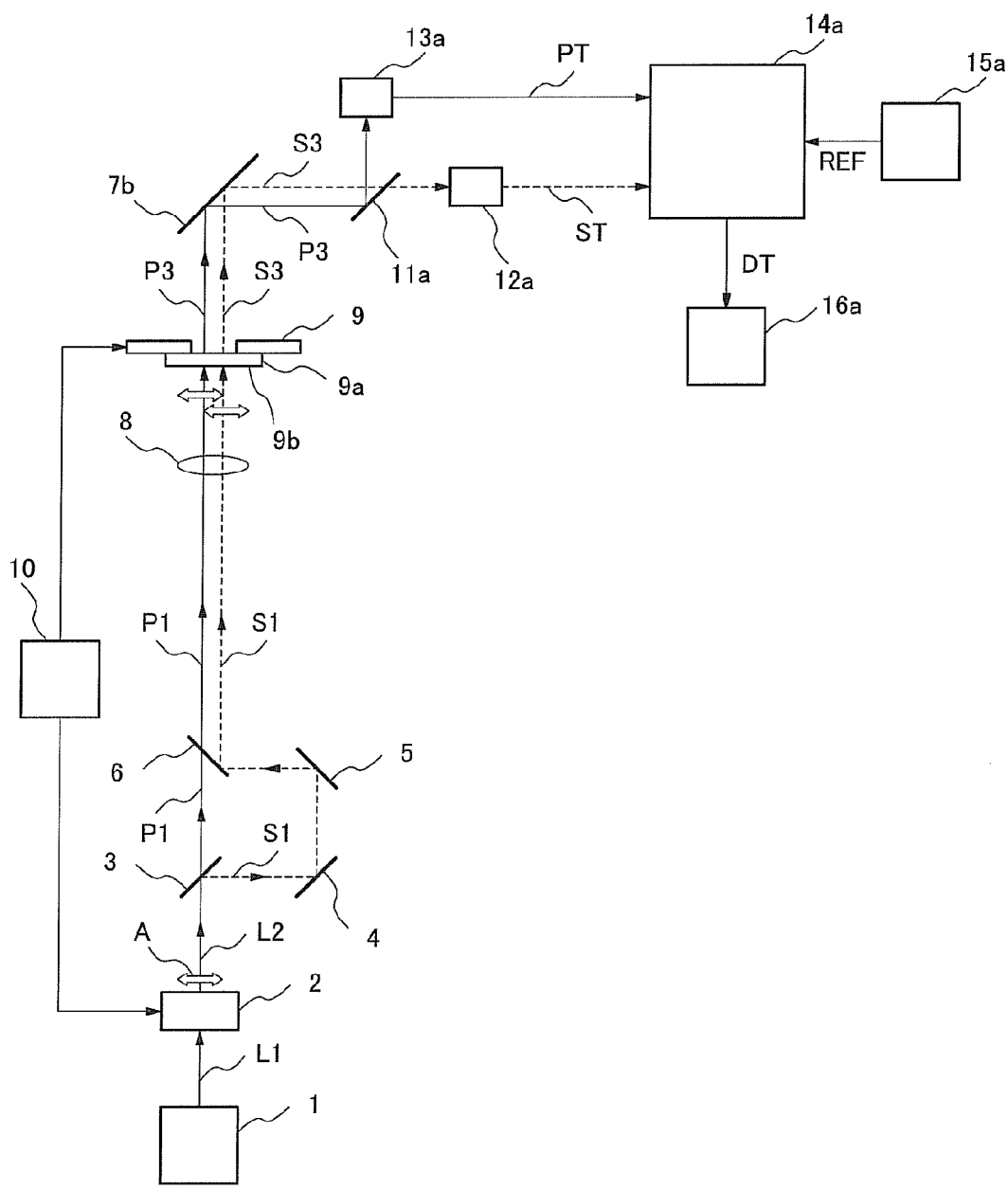
FIG. 7 is a block diagram showing a schematic configuration of a defect inspecting apparatus for a fine structural object according to a second exemplary embodiment of the present invention.

FIG. 7 is a block diagram showing a schematic configuration of a defect inspection apparatus to inspect a defect of a fine structural object according to a second exemplary embodiment of the present invention. The major difference of the defect inspection apparatus according to the second exemplary embodiment of the present invention from that according to the first exemplary embodiment of the present invention is that a scanning type transmission microscope method in which a transmission image of an inspection object is used instead of a reflection image of the inspection object is adopted. That is, the defect inspection apparatus according to the second exemplary embodiment of the present invention photographs the transmission image and inspects whether or not a defect in the inspected area exists. According to the second exemplary embodiment of the present invention, in order to realize the scanning type transmission microscope method, a mirror corresponding to a transmission optical system is employed as shown in FIG. 7 instead of the semi-transparent mirror 7 and the split mirror 11 shown in FIG. 1 which are included in the optical reflection system. Further, each unit which is identical to the constituent shown in FIG. 1 has the same reference number in FIG. 7 as the constituent has, and description thereof are omitted. Moreover, each unit which is corresponding to the constituent in FIG. 1 has a subscript to make the relationship clear and descriptions thereof are omitted. The three signals shown in FIG. 7, a p-reflection image detecting signal PT, an s-reflection image detecting signal ST and a measured result DT, correspond to the p-reflection image detecting signal PR, the s-reflection image detecting signal SR and the inspection result DR respectively of the first exemplary embodiment shown in FIG. 1.

The defect inspection apparatus according to the second invention of the present invention makes the same effect as that of the first exemplary embodiment of the present invention. That is, since the nonsimultaneous double-scanning (FIG. 4) is carried out by using the light converging spot Px of the p-polarized light and the light converging spot Sx of the s-polarized light, the p-polarized light transmission image reflecting property of the p-polarized light and the s-polarized light transmission image reflecting property of the s-polarized light are photographed. In the defect inspection, after the p-polarized light pass-through image photographed using the p-polarized light and the s-polarized light pass-through image photographed using the s-polarized light are compared, one transmission image having higher resolving power than that of the other transmission image is adopted. Accordingly, whether or not a defect of a shape of the inspection object (fine structural object) 9b and a foreign object attached to the inspection object 9b exist is inspected with high resolution and high sensitivity.

Further, it is possible to judge whether or not a defect exists with the naked eye, like the first exemplary embodiment of the present invention. Moreover, the image processing system 14a, the reference image storing unit 15a and the inspection data storing unit 16a can be replaced by an external processing apparatus. In such a case, the image processing system 14a, the reference image storing unit 15a and the inspection data storing unit 16a can be omitted from the defect inspection apparatus shown in FIG. 7. Moreover, the p-reflection image detecting signal PT and the s-reflection image detecting signal ST enter a display apparatus or an external processing apparatus, and then, displaying or signal processing is performed.

Moreover, the p-polarized light beam P1 and the s-polarized light beam S1 can be entered from outside, like the first exemplary embodiment of the present invention. When the required resolving power is low, the objective lens 8 is also unnecessary. When the inspection area is small, it is possible to inspect a defect only by the scanning using the deflection scanning means 2. It is possible to output the reflection light P2 and S2 as a light signal without photoelectrical conversion.

Accordingly, the minimum configuration of the defect inspection apparatus according to the exemplary embodiment of the present invention includes the deflection scanning means 2 and the semi-transparent mirror 7b.

3. Third Exemplary Embodiment

Figure 8:
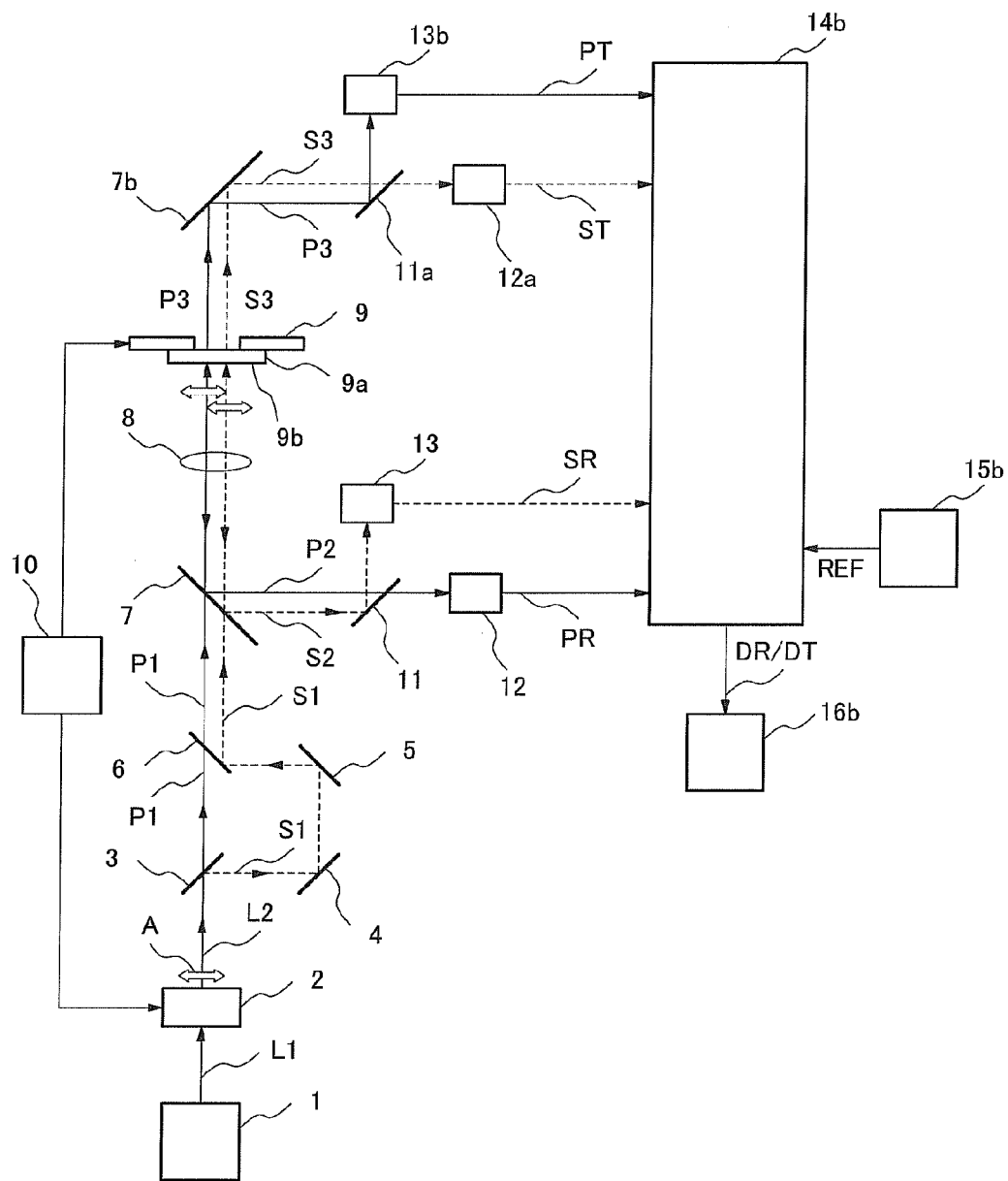
FIG. 8 is a block diagram showing a schematic configuration of a defect inspecting apparatus for a fine structural object according to a third exemplary embodiment of the present invention.

FIG. 8 is a block diagram showing a schematic configuration of a defect inspection apparatus to inspect a defect of a fine structural object according to a third exemplary embodiment of the present invention. Both the reflection image and the transmission image of the inspection object can be photographed by combining the first and the second exemplary embodiments of the present invention as shown in FIG. 8, according to the defect inspection apparatus of the exemplary embodiment of the present invention. Furthermore, each unit shown in FIG. 8 which is identical to the constituent shown in FIGS. 1 and 7 has the same reference number as the constituent has, and descriptions thereof are omitted. Moreover, each unit which corresponds to the constituent in FIGS. 1 and 7 has a subscript to make the relationship clear and descriptions thereof are omitted.

The defect inspection apparatus according to the third exemplary embodiment of the present invention carries out the nonsimultaneous double-scanning (FIG. 4) using the light converging spot Px of the p-polarized light and the light converging spot Sx of the s-polarized light, like the first and the second exemplary embodiments of the present invention. Moreover, according to the defect inspection apparatus of the third exemplary embodiment of the present invention, four kinds of inspection images, that is, the p-polarized light reflection image reflecting property of the p-polarized light, the p-polarized light transmission image reflecting property of the p-polarized light, the s-polarized light reflection image reflecting property of the s-polarized light and the s-polarized light transmission image reflecting property of the s-polarized light can be photographed simultaneously. Therefore, the defect inspection apparatus according to the third exemplary embodiment of the present invention can cope with a case in which the resolving power of the transmission image is higher than that of the reflection image and a case in which the resolving power of the reflection image is higher than that of transmission image. In the defect inspection apparatus of the third exemplary embodiment of the present invention, it is possible to compare four images, that is, the p-polarized light reflection image photographed using the p-polarized light, the p-polarized light transmission image photographed using the p-polarized light, the s-polarized light reflection image photographed using the s-polarized light, and the s-polarized light transmission image photographed using the s-polarized light in the defect inspection process. Accordingly, whether or not a defect of a shape of the inspection object (fine structural object) 9a and a foreign object attached to the inspection object 9a exist is inspected with high resolving power and high sensitivity, since the image with the highest resolving power is employed.

Further, it is possible to judge whether or not a defect exists with the naked eye like the first and the second exemplary embodiments of the present invention. The image processing system 14b, the reference image storing unit 15b and the inspection data storing unit 16b may be replaced by an external processing apparatus. In such cases, the image processing system 14b, the reference image storing unit 15b and the inspection data storing unit 16b can be omitted from the defect inspection apparatus shown in FIG. 8. Moreover, the p-reflection image detecting signals PR and PT and the s-reflection image detecting signals SR and ST enter a display apparatus or an external processing apparatus, and displaying or signal processing is performed.

Moreover, the p-polarized light beam P1 and the s-polarized light beam S1 can be inputted from outside, like the first and the second exemplary embodiments of the present invention. When the required resolving power is low, the objective lens 8 is also unnecessary. When the inspection area is small, it is possible to inspect a defect only with the scanning by the deflection scanning means 2. It is possible to output the reflection light P2 and S2 as a light signal without photoelectrical conversion.

Accordingly, the minimum configuration of the defect inspection apparatus according to the exemplary embodiment of the present invention includes the deflection scanning means 2 and the semi-transparent mirrors 7 and 7b.

4. Fourth Exemplary Embodiment

A defect inspection apparatus according to a fourth exemplary embodiment of the present invention will be described below. According to the defect inspection apparatus of the fourth exemplary embodiment of the present invention, the p-polarized light beam P1 and the s-polarized light beam S1 are overlapped completely, and the overlapped two kinds of polarized light beams scan the same inspection area set on an inspection object surface of a fine structural object at one time. Accordingly the fourth exemplary embodiment of the present invention is different from the first to the third exemplary embodiment in which the double-scanning is carried out while the p-polarized light beam P1 and the s-polarized light beam S1 are separated from each other in parallel by a distance approximately corresponding to the scanning width W in a scanning direction.

The defect inspection apparatus according to the fourth exemplary embodiment of the present invention employs a polarized light splitting optical system as an optical means which splits a reflection light into a reflection light of the p-polarized light and a reflection light of the s-polarized light and detects the split light, instead of the split mirror 11 (FIG. 2A) of the confocal optical system. As the polarized light splitting optical system, for example, a polarized light beam splitter 11c is employed, which reflects the reflection light P2 of the p-polarized light and allows the reflection light S2 of the s-polarized light to pass through, as shown in FIG. 2B.

The defect inspection apparatus according to the fourth exemplary embodiment of the present invention can also obtain the same effect as that of the first exemplary embodiment of the present invention. However, in the defect inspection apparatus employing the polarized light beam splitter 11c, a polarization state is disordered due to light scattering which is generated at an edge part of a pattern or the like depending on a shape and a size of the pattern. Therefore, cross talk such as a reflection light component PN of the p-polarized light and a reflection light component SN of the s-polarized light may be generated as shown in FIG. 2B. That is, the p-polarized light reflection image intrudes into the s-polarized light reflection image, and vice versa. The intruding images may cause an error. In particular, when a deep pattern with relatively narrow width is inspected, the first exemplary embodiment of the present invention is preferable. The p-polarized light beam P1 and the s-polarized light beam S1 independently can be used for dependent scanning and can be split spatially, since the first exemplary embodiment of the present invention employs the confocal optical system.

5. Fifth Exemplary Embodiment

Figure 9:
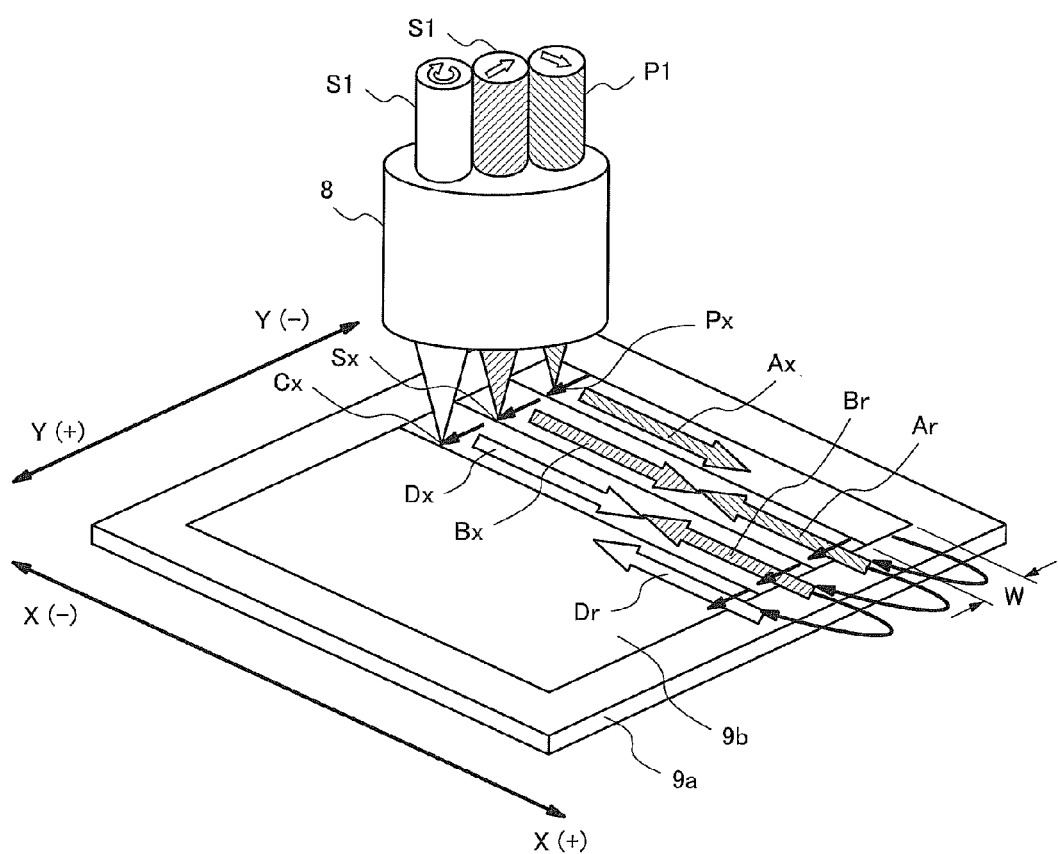
FIG. 9 is a perspective view showing schematically a nonsimultaneous double-scanning operation of a defect inspecting apparatus for a fine structural object using a p-polarized light and an s-polarized light according to a fifth exemplary embodiment of the present invention.

A fifth exemplary embodiment of the present invention will be described below with reference to FIG. 9. According to the fifth exemplary embodiment of the present invention, a simultaneous scan is carried out by three beams, that is, a p-polarized light beam P1, an s-polarized light beam S1 and a circularly polarized light beam C1. As a result, the defect inspection apparatus according to the fifth exemplary embodiment of the present invention can carry out a nonsimultaneous double-scanning. That is, according to the configuration, a simultaneous split beam scanning is carried out with three kinds of polarized light spots including the light converging spot Px of the p-polarized light, the light converging spot Sx of the s-polarized light and the circularly polarized light spot Cx of the circularly polarized light C2, in directions indicated by arrows Ax, Bx and Dx respectively. At each of three kinds of the polarized light spots, images of three inspection areas which are away from each other approximately by the scanning width W in the scanning direction Y(+) are photographed. Each of the light converging spots Px, Sx and Cx moves in the direction Y(+) approximately by a distance of the scanning width W step-by-step, and performs scanning in a meandering fashion. As a result, the defect inspection apparatus according to the fifth exemplary embodiment of the present invention can photograph three kinds of images including the p-polarized light image, the s-polarized light image and the circularly polarized light image in a common inspection area among the light converging spots Px, Sx, and Cx, and can carry out the inspection.

Meanwhile, utilizing the circularly polarized light beam C1, the defect inspection apparatus according to the fifth exemplary embodiment of the present invention cannot carry out splitting based on a difference in the direction of polarization of the polarized light. Accordingly, each of the polarized light beams is split by a mirror or the like at a position where each of the polarized light beams is split spatially. As mentioned above, the defect inspection apparatus according to the fifth exemplary embodiment of the present invention can obtain simultaneously an average image (circularly polarized light image) with respect to the polarized light, by using the circularly polarized light. Therefore, the defect inspection apparatus according to the fifth exemplary embodiment of the present invention can obtain information on the image specific to the linearly polarized light, through calculating difference between the circularly polarized light image and the p-polarized light image or the s-polarized light image.

6. Sixth Exemplary Embodiment

Figure 10:
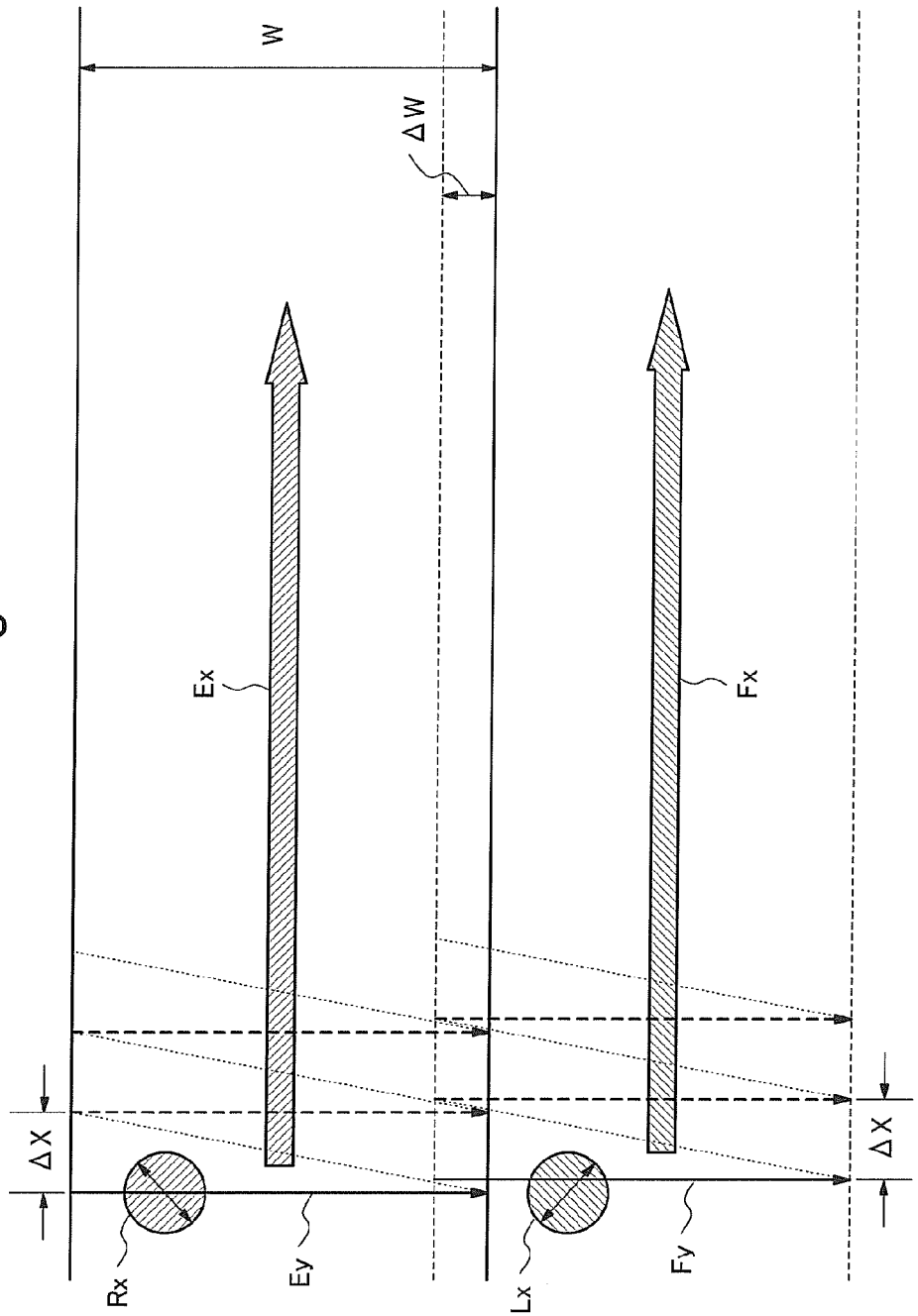
FIG. 10 is a plan view showing a double-scanning operation of a defect inspecting apparatus for a fine structural object according to a sixth exemplary embodiment of the present invention.

A defect inspection apparatus according to a sixth exemplary embodiment of the present invention will be described below with reference to FIG. 10. In the defect inspection apparatus of the first to the fifth exemplary embodiments of the present invention, an angle which a direction of polarization (a direction of a polarization plane of a linearly polarized light) forms with a beam scanning direction is 0 degree or 90 degrees. The defect inspection apparatus according to the sixth exemplary embodiment of the present invention outputs an inclined p-polarized light beam Rx and an inclined s-polarized light beam Lx each having a polarization plane which tilts at 45 degrees to the beam scanning direction and is orthogonal to another polarization plane and photographs an image. The defect inspection apparatus according to the sixth exemplary embodiment of the present invention can meet inspection of the inspection object having a fine pattern which is arranged in an oblique direction. Further, the angle of the polarization plane of the linear polarization with respect to the beam scanning direction is not limited to 45 degrees. The angle of the polarization plane may be selected optionally according to the direction of the fine pattern of the inspection object.

The exemplary embodiments of the present invention are described in detail with reference to drawings as the first to sixth exemplary embodiments of the present invention. A specific configuration is not limited to the above mentioned exemplary embodiments, and even if any design changes are made in a range that does not deviate from a point of the present invention, such changed configurations are included in the present invention. For example, the number of polarization property of the scanning beam and the number of the polarized light spots are not limited to the numbers illustrated in the above-mentioned exemplary embodiments and may be changed optionally.

For example, the polarization property of the scanning beam may include a circularly polarized light and a third and a fourth linearly polarized lights each having a polarization plane which tilts at a predetermined angle, for example, at 45 degrees to the beam scanning direction and which is orthogonal to another polarization plane. Further, the number of the polarization spots may be 3. The polarization property of the scanning beam may include the circularly polarized light, a first linearly polarized light having a polarization plane parallel to the beam scanning direction, a second linearly polarized light having a polarization plane orthogonal to the beam scanning direction, and the third and fourth linearly polarized lights each having a polarization plane which tilts at a predetermined angle, for example, at 45 degrees to the beam scanning direction and which is orthogonal to another polarization plane. Then, the number of the light spots is 5.

It is possible to photograph a scattering image to use the scattering image for the inspection, in addition to the transmission image and the reflection image. As an optical microscope system which photographs the scattering image, the reflection type optical microscope system as shown in FIG. 1 may be used, and the transmission type optical microscope system as shown in FIG. 7 may be used. The pure scattering image can be photographed, for example, through mounting a shading means to block the reflection light and the transmission light off. Furthermore, images including at least two kinds of images among the reflection image, the transmission image and the scattering image can be used for the inspection.

Some of automatic focusing systems employ a reflection light of the inspection light. The optical automatic focusing system advantageously includes high focusing precision and fast focus controlling. However, since the reflection light may include an error ingredient depending on a fine shape pattern as the inspection object, a focusing error may be caused. In the exemplary embodiments of the present invention, patterns observed by the p-polarized light and the s-polarized light are originally different from each other, and a pattern suitable for the respective polarized light is selected. Therefore, it is also possible to obtain focus signals by both the p-polarized light and the s-polarized light, and to carry out the focusing control based on one focus signal which includes less fluctuation.

7. Seventh through Eleventh Exemplary Embodiment

According to a defect inspection apparatus of a seventh exemplary embodiment of the present invention, it is noticed that a close relation between polarization property and resolving power exists. The defect inspection apparatus of the seventh exemplary embodiment of the present invention includes a light beam splitting means which splits a light beam outputted by a light source into N (N is natural number not smaller than 2) polarized light beams each of which includes different property, a scanning means which scans an inspection area set on a surface of an inspection object by using each of the polarized light beams, a scanning control means which controls a drive mechanism of the scanning means and a XY stage to scan sequentially the same inspection area set on the surface of the inspection object by using each of polarized light beams by the scanning means and consequently and to totally carry out N times multiple-scanning, a detection signal generating means which receives a reflection light reflected by the inspection area, a transmission light which passes the inspection area, or a scattering light scattered by the inspection area, any two light among the reflection light, the pass-through light and the scattering light, or all of these lights, converts the receiving light into an electric signal and generates a detection signal, and an image processing means which photographs a plurality of images which reflect the inspection area of the surface of the inspection object, that is, N reflection images, N transmission images, N scattering images, or M×N images (M is 2 or 3) corresponding to images of any two kinds or all kinds of the above images by using the detection signal outputted by the detecting signal generation means and which inspects existence of a defect of the fine structural object.

The above-mentioned scanning control means includes a configuration in which each of the polarized light beams scan the same inspection area in sequence with a scanning means and N times multiple-scanning is totally performed. Instead of the configuration above, the scanning control means may include a configuration in which overlapped N polarized light beams scan the same inspection area set on the surface of the inspection object at one time with the scanning means.

A defect inspection method according to an eighth exemplary embodiment of the present invention is a method to inspect a defect of a fine structural object in order to inspect whether or not a defect of the fine structural object exists with a light beam. According to the method, a light beam outputted from a light source is split into N (N is natural number not smaller than 2) polarized light beams each of which includes different property and the same inspection area set on a surface of an inspection object of the fine structural object is scanned sequentially with each of the polarized light beams, that is, is totally multiple-scanned N times. Then, a plurality of images which reflect the inspection area of the surface of the inspection object, that is, N reflection images, N transmission images, N scattering images, or M×N images (M is 2 or 3) corresponding to images of any two kinds or all kinds of the above images are photographed and it is inspected whether or not the fine structural object includes any defect.

A defect inspection method according to a ninth exemplary embodiment of the present invention is a method to inspect a defect of a fine structural object in order to inspect whether or not a defect of the fine structural object exists with a light beam. According to the method, a light beam outputted from a light source is split into N (N is natural number not smaller than 2) polarized light beams each of which includes a different property. Then, after N polarized light beams are overlapped, the overlapped N polarized light beams scan the same inspection area set on a surface of an inspection object of the fine structural object at one time. Consequently, a lot of images which reflect the inspection area of the surface of the inspection object, that is, N reflection images, N transmission images, N scattering images, or M×N images (M is 2 or 3) corresponding to images of any two kinds or all kinds of the above images are photographed and it is inspected whether or not the fine structural object includes any defect.

A defect inspection apparatus according to a tenth exemplary embodiment of the present invention is an apparatus to inspect whether or not a defect of a fine structural object exists with light beam. The defect inspection apparatus includes a XY stage which mounts a fine structural object thereon and move it, a light source which outputs a light beam, a light beam splitting means which splits a light beam outputted by a light source into N (N is natural number not smaller than 2) polarized light beams each of which includes different property, a scanning means which scans an inspection area set on a surface of an inspection object by using each of the polarized light beams, a scanning control means which controls a drive mechanism of the scanning means and the XY stage to scan sequentially the same inspection area set on the surface of the inspection object by using each of polarized light beams by the scanning means and consequently and to totally carry out N times multiple-scanning, a detection signal generating means which receives a reflection light reflected by the inspection area, a transmission light which passes the inspection area, or a scattering light scattered by the inspection area, any two light among the reflection light, the pass-through light and the scattering light, or all of these lights above, converts the receiving light into an electric signal and generates a detection signal, and an image processing means which photographs a plurality of images which reflect the inspection area of the surface of the inspection object, that is, N reflection images, N transmission images, N scattering images, or M×N images (M is 2 or 3) corresponding to images of any two kinds or all kinds of the above images by using the detection signal outputted by the detecting signal generation means and which inspects existence of a defect of the fine structural object.

A defect inspection apparatus according to an eleventh exemplary embodiment of the present invention is an apparatus to inspect whether a defect of a fine structural object exists with light beam. The defect inspection apparatus includes a XY stage on which the fine structural object is put to be moved, a light source which outputs a light beam, a light beam splitting means which splits the light beam into N (N is natural number not smaller than 2) polarized light beams each of which includes different property, a scanning means which overlaps the N polarized light beams and scans an inspection area set on a surface of an inspection object at one time by using the overlapped N polarized light beams, a detection signal generating means which receives a reflection light which is reflected by the inspection area, a transmission light which passes the inspection area, a scattering light which is scattered by the inspection area, any two lights among the reflection light, the transmission light and the scattering light, or all of the reflection light, the transmission light and the scattering light, converts the receiving light into an electric signal and generates a detection signal, and an image processing means which photographs a plurality of images which reflect the inspection area of the surface of the inspection object, that is, N reflection images, N transmission images, N scattering images, or M×N images (M is 2 or 3) corresponding to images of any two kinds or all kinds of the above images by using the detection signal outputted by the detecting signal generation means, and inspects existence of defect of the fine structural object.

Miniaturization in a shape or a structure of a fine structural object such as the reticle, the photomask, LSI or MEMS proceeds. As the miniaturization proceeds, optical property (reflection ratio, transmissivity and scattering intensity) of an inspection object surface of the fine structural object becomes different depending on polarization light property of an illuminating light. The particle measuring apparatus disclosed in the patent document uses only two kinds of the linearly polarized light, that is, the p-polarized light and the s-polarized light of which directions of polarization are orthogonal to each other. Therefore, the particle measuring apparatus cannot cope with inspection of further miniaturized fine structural object from the point of view of sensitivity and resolution. Moreover, in the particle measuring apparatus, the p-polarized light and the s-polarized light illuminate the same inspection area which is set on the surface of the inspection object of the fine structural object simultaneously. Therefore, as the miniaturization proceeds, it is expected that the particle measuring apparatus cannot certainly split and detect the reflection light of the p-polarized light and the reflection light of the s-polarized light depending on a shape and a pattern of the fine structural object. In such case, it is expected that a reflection image with high resolution cannot be obtained.

According to the defect inspection method or the defect inspection apparatus of the seventh to the eleventh exemplary embodiments of the present invention, it is possible to select the image with high sensitivity and high resolution formed by the polarized light beam among a plurality of images formed by using of a plurality of polarized light beams each of which includes different polarization property, based on a shape and a size of the fine pattern. Therefore, it is possible to improve the optical resolving power. Moreover, scanning with light beams each of which includes different polarization property is carried out simultaneously. Therefore, it is possible to improve optical resolving power without degradation of throughput. According to the exemplary embodiments of the present invention, it is possible to realize the defect inspection apparatus with not extensive but relatively simple modification to the beam scan type apparatus.

The present invention can be applied to inspection of a foreign object which is put on an original mask plate having a fine structure such as especially, a liquid crystal display panel, or a mask and a reticle which are used on copying a circuit such as semiconductor circuit, and to inspection of a defect in a manufacturing process. Additionally, the present invention can also be applied to the optical inspection of MEMS, the electronic device or the like which includes the fine structural object.

While the invention has been particularly shown and described with reference to exemplary embodiments thereof, the invention is not limited to these exemplary embodiments. It will be understood by those of ordinary skill in the art that various changes in form and details may be made therein without departing from the spirit and scope of the present invention as defined by the claims.

Further, it is the inventor's intention to retain all equivalents of the claimed invention even if the claims are amended during prosecution.

What is claimed is:

1. A defect inspection method which acquires an image of a fine structure object surface and carriers out defect inspection, comprising:
    splitting a light beam output from a light source into N polarized light beams which are mutually spatially separated, where N is a natural number equal to or greater than two; and,
    illuminating sequentially a surface of the object arranged in the same shooting area using each of the N polarized light beams, including at least two polarized light beams have polarization directions orthogonal to one another, and a cross-sectional shape perpendicular to an optical axis of each polarized light beam is in an elliptical shape, which is formed by entering in parallel with an optical axis of a lens with high 0.8, which is a numerical aperture of the lens, and being converged, in the polarization direction thereof.

2. The method according to claim 1, wherein,
    the scanning is carried out along a predetermined scanning line; and
    a position of the scanning line is moved onto another line parallel to the scanning line on completion of the scanning along the scanning line.

3. The method according to claim 2, wherein,
    the N polarized light beams which are separated each other by a scanning width corresponding to length of the scanning line are radiated to the surface.

4. The method according to claim 2, wherein,
    the N polarized light beams include a first linearly polarized light beam of which direction of polarization is parallel to the scanning line and a second linearly polarized light beam of which direction of polarization is orthogonal to the scanning line.

5. The method according to claim 2, wherein,
    the N polarized light beams include a third and a fourth linearly polarized light beams of which directions of polarization tilt at a predetermined angle except zero degree with respect to the scanning line direction and which are orthogonal to each other.

6. The method according to claim 2, wherein,
the N polarized light beams include a first linearly polarized light beam of which direction of polarization is parallel to the scanning line, a second linearly polarized light beam of which direction of polarization is orthogonal to the scanning line and a third and a fourth linearly polarized light beams of which directions of polarization are tilt at a predetermined angle except zero degree with respect to the scanning line direction and which are orthogonal to each other.

7. The method according to claim 1, further comprising:
comparing N images of a first object which are formed based on the image signal and correspond to the scanning carried out using the each of N polarized light beams, with N images of a second object which are formed based on the image signal and correspond to the scanning carried out using the each of N polarized light beams, and
forming a differential image based on a result of the comparing.

8. The method according to claim 1, further comprising:
comparing N images which are formed based on the image signal and correspond to the scanning carried out using the each of N polarized light beams with a reference image based on design data of the object, and
forming a differential image based on a result of the comparing.

9. The method according to claim 1, wherein,
each of the reflected N polarized light beams, each of the passed-through N polarized beams or each of the scattered N polarized beams is split spatially using a polarized light splitting optical system.

10. The method according to claim 1, wherein,
the object includes a reticle having a pattern, a photo-mask having a pattern, an element made using the reticle or the photo-mask.

11. A defect inspection apparatus, comprising:
moving unit mounting an object thereon and moving the object;
light source outputting a light beam;
light beam splitter splitting the light beam into N (N is natural number equal to or more than two) polarized light beams which are mutually spatially separated, the N polarize light beams including at least two polarized light beams have polarization directions orthogonal to one another, and a cross-sectional shape of each polarized light beam is in an elliptical shape, which is formed by entering in parallel with an optical axis of a lens with high 0.8, which is a numerical aperture of the lens, and being converged, in the polarization direction thereof.

12. The defect inspection apparatus according to claim 11, further comprising:
image forming unit for forming N images corresponding to the scanning carried out using the each of N polarized light beams based on the image signal.

13. The defect inspection apparatus according to claim 12, wherein,
the image forming unit compares N images of a first object which are formed based on the image signal and correspond to the scanning carried out using the each of N polarized light beams, with N images of a second object which are formed based on the image signal and correspond to the scanning carried out using the each of N polarized light beams, and forms a differential image based on a result of the comparing.

14. The defect inspection apparatus according to claim 12, wherein,
the image forming unit compares N images which are formed based on the image signal and correspond to the scanning carried out using the each of N polarized light beams with a reference image based on design data of the object, and forms a differential image based on a result of the comparing.

15. The defect inspection apparatus according to claim 12, wherein,
the scanning unit allows the N polarized light beams separated each other by scanning width corresponding to length of the scanning line to radiate to the surface.

16. The defect inspection apparatus according to claim 12, wherein,
the N polarized light beams include a first linearly polarized light beam of which direction of polarization is parallel to the scanning line and a second linearly polarized light beam of which direction of polarization is orthogonal to the scanning line.

17. The defect inspection apparatus according to claim 16, wherein, the N polarized light beams include a circularly polarized light beam.

18. The defect inspection apparatus according to claim 12, wherein,
the N polarized light beams include a third and a fourth linearly polarized light beams of which directions of polarization tilt at a predetermined angle except zero degree with respect to a the scanning line direction and which are orthogonal to each other.

19. The defect inspection apparatus according to claim 18, wherein, the N polarized light beams include a circularly polarized light beam.

* * * * *